US011974731B2

(12) United States Patent
Sun et al.

(10) Patent No.: US 11,974,731 B2
(45) Date of Patent: May 7, 2024

(54) AUTOMATIC THROAT SWAB SAMPLING SYSTEM

(71) Applicant: Tsinghua University, Beijing (CN)

(72) Inventors: Fuchun Sun, Beijing (CN); Bin Fang, Beijing (CN); Huaping Liu, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 568 days.

(21) Appl. No.: 17/325,620

(22) Filed: May 20, 2021

(65) Prior Publication Data

US 2021/0369252 A1 Dec. 2, 2021

Related U.S. Application Data

(63) Continuation of application No. PCT/CN2020/111407, filed on Aug. 26, 2020.

(30) Foreign Application Priority Data

May 26, 2020 (CN) ........................ 202010452755.0

(51) Int. Cl.
*A61B 10/00* (2006.01)
*A61B 5/1171* (2016.01)
*A61B 90/00* (2016.01)

(52) U.S. Cl.
CPC ........ *A61B 10/0051* (2013.01); *A61B 5/1176* (2013.01); *A61B 90/06* (2016.02); *A61B 2090/062* (2016.02); *A61B 2562/0247* (2013.01)

(58) Field of Classification Search
None
See application file for complete search history.

(56) References Cited

PUBLICATIONS

Haddadin et al. Autonomous swab robot for naso and oropharyngeal COVID-19 screening; Scientific Reports | (2024) 14:142 | Nature Portfolio (Year: 2024).*

(Continued)

*Primary Examiner* — Jay B Shah
(74) *Attorney, Agent, or Firm* — WPAT, PC

(57) ABSTRACT

The invention proposes an automatic throat swab sampling system, which comprises an automatic to-be-tested person identity information checking and collection prompting unit, a to-be-tested person head positioning unit, a navigation positioning unit which enters the oral cavity of a to-be-detected person along with the tail end of the sample collection execution unit for collecting a throat image and determining depth information between a depth sensor and the throat of the to-be-detected person, a sample collection execution unit including a three-degree-of-freedom guide rail type device and a one-degree-of-freedom end execution mechanism, an automatic throat swab loading and unloading unit and a remote monitoring unit which are arranged on a working platform. In a throat swab collecting process, the real-time information of all units communicates with the remote monitoring unit, and medical staff monitors the collected person and all the units in real time through a computer in a remote safety room, so that measures can be taken timely to guarantee the safety and effectiveness of the whole process when an accident occurs. The system realizes the full-automatic throat swab collection process.

6 Claims, 4 Drawing Sheets

700 600 300 102 800 100 400 103 101

(56) References Cited

PUBLICATIONS

Chen et al. A collaborative robot for COVID-19 oropharyngeal swabbing; Robotics and Autonomous Systems 148 (2022) (Year: 2022).*
Li et al. Clinical application of an intelligent oropharyngeal swab robot: implication for the COVID-19 pandemic; Eur Respir J 2020; 56 (Year: 2020).*

* cited by examiner

AUTOMATIC THROAT SWAB SAMPLING SYSTEM

CROSS REFERENCE TO RELATED APPLICATION

The invention falls into the field of medical robots, and specifically relates to an automatic throat swab sampling system.

BACKGROUND OF THE INVENTION

The novel coronavirus pneumonia epidemic has been spreading around the world. The virus infection detection means mainly focus on collecting samples from throat swabs for nucleic acid tests, which is a process with a very high risk of infection and requires certain operative skills. During the sampling, the patient needs to open his mouth to expose the throat, which is the area where the virus is relatively concentrated as the patient can produce a large number of droplets or aerosols by forced breathing and coughing. At present, most sampling rooms are enclosed areas of about 10 square meters, with a relatively high aerosol concentration. The sampling medical staff who collect throat swabs at close range are at a higher risk of cross-infection even with three-grade defense (protective clothing, goggles and gloves). During the outbreak of novel coronavirus pneumonia, the medical staff need to wear comprehensive protective equipment for a long time as there are many infected persons, resulting in excessive work intensity and long working hours. In addition, due to the difference in the skills of medical staff at different levels, psychological fear, fatigue of medical staff and other factors in the process of collecting throat swabs, throat swab collection operation can easily lead to difference in swab quality to be false-negative, which affects the judgment on pathogenetic condition.

As throat swab collection is necessary for the detection of virus types and is at a high risk of infection with viruses similar to the novel coronavirus, it is urgent to use the robot technology to replace medical staff for autonomous sampling, thereby reducing the workload and the risk of infection of the medical staff, which also bear great significance in treatment of war wound, disaster assistance as well as prevention and control of infectious diseases.

SUMMARY OF THE INVENTION

To overcome the defects in the prior art, the invention proposes an autonomic throat swab sampling system, which realizes full automation of checking information of the collector, collecting throat swab, sealing and the like by the medical staff during the collection process, and can effectively reduce the workload and infection risk of medical staff.

To achieve the objective, the invention adopts the following technical solution:

The autonomic throat swab sampling system proposed by the invention includes an automatic to-be-tested person identity information checking and collection prompting unit, a to-be-tested person head positioning unit, a navigation positioning unit, a sample collection execution unit, an automatic throat swab loading and unloading unit and a remote monitoring unit which are arranged on a working platform, where:

the automatic to-be-tested person identity information checking and collection prompting unit includes an electronic screen, and the facial features of the to-be-tested person are acquired through a front camera of the electronic screen, and are compared with the identity information of the to-be-tested person for face recognition; the information of the to-be-tested person is shown to the tested person through the electronic screen for confirmation, the to-be-tested person is guided by voice and text prompts to enter automatic throat swab collecting equipment after confirmation, and the operating procedures and precautions are reported;

the to-be-tested person head positioning unit includes a head positioning frame, through which the head of the to-be-tested person is fixed, and a mouthpiece fixedly arranged thereon, where the mouthpiece is positioned at comfortable height of the to-be-tested person by adjusting a distance between the mouthpiece and the working platform; the mouthpiece is made of a disposable consumable, and is used for opening the oral cavity and flattening the tongue of the to-be-tested person to provide a clear space extending to the throat.

The navigation positioning unit includes a depth sensor fixed at the tail end of the sample collection execution unit, which enters the oral cavity of the to-be-tested person along with the sample collection execution unit to collect a throat image and determine depth information between the depth sensor and the throat of the to-be-tested person;

the sample collection execution unit includes a three-degree-of-freedom guide rail type device and a one-degree-of-freedom end execution mechanism, where the three-degree-of-freedom guide rail type device is a gantry type three-axis mechanism having X, Y and Z axes in a width direction of the oral cavity, a depth direction of the oral cavity and a planar direction perpendicular to the working platform; the gantry type three-axis mechanism includes an X-axis module, two Y-axis modules which are fixedly arranged on the working platform at intervals and a Z-axis module, the Y-axis module, the X-axis module and the Z-axis module are sequentially connected and linked with one another; the depth sensor in the navigation positioning unit and the tail end execution mechanism are fixedly arranged on the Z-axis module; and the action of wiping the throat of the to-be-tested person is controlled by the X-axis module and the Z-axis module, and the feeding motion into the oral cavity of the to-be-tested person and the axial feeding motion of the wiping action force control part are controlled by the Y-axis module;

the automatic throat swab loading and unloading unit includes a six-degree-of-freedom mechanical arm which is controlled to reach the designated position of the throat swab and a tail end gripping claw which is opened and closed to grip the throat swab; and the six-degree-of-freedom mechanical arm gripping the throat swab is controlled to load to the tail end execution mechanism in the sample collection execution unit;

the remote monitoring unit includes a master control system in which an information base of the to-be-tested person is stored, where a second control chip, which communicates with the PC through a RS-485 interface is integrated on a second control board in a PC of the master control system; the automatic to-be-tested person identity information checking and collection prompting unit and the automatic throat swab loading the unloading unit connect with the PC of the master control system through a TCP network; the to-be-tested person identity information base in the master control system accomplishes the checking confirmation of person information by the automatic to-be-tested person identity information checking and collection prompting unit; the navigation positioning unit is connected to the PC of the master control system through USB for transmitting collected image and depth information of the depth sensor onto the PC of the master control system; the location information of tonsil at the two sides in the oral cavity of the to-be-tested person is accurately calculated after the image and depth information collected by the depth sensor is denoised while compensated through a mean filter algorithm, and then is subjected to coordinate conversion for being matched with a coordinate system of the sample collection execution unit which is guided to the location to collect samples; the guide rail type device in the sample collection execution unit is separately connected to the PC of the master control system through a RS-485 interface and a GPIO interface; the second control chip performs multi-task dispatch needed for motion calculation and trajectory tracking of the gantry type three-axis mechanism, where the dispatch processes and converts the image and depth information collected by the depth sensor into mechanical motion of the gantry type three-axis mechanism in real time, and sends a corresponding control signal to the module of each axis in the sample collection execution unit through the GPIO interface; and the tail end execution mechanism in the sample collection execution unit is connected to the PC of the master control system through a serial interface to obtain the real-time state of the tail end execution mechanism.

The invention has the following features and beneficial effects:

The system can automatically accomplish the throat swab sampling process with a high degree of automation, specifically: (1) during the sampling process, the patient's identity information is automatically checked and confirmed; (2) the throat swab is automatically loaded and unloaded, which can be seamlessly connected to an external sampling tube labeling system, a conveying system, and a sorting system; (3) the autonomous trajectory planning and execution of the sampling action is simple to operate by ordinary remote on-duty personnel, saving the manpower of professional medical staff. In addition, the system also has a flexible control sampling function to avoid hard stimulation on the throat tissue of the to-be-tested person.

DETAILED DESCRIPTION OF THE PREFERRED EMBODIMENTS

In order to clarify the objectives, technical solutions, and advantages of the invention, the followings further describe the invention in detail with reference to the accompanying drawings and embodiments. It should be understood that the specific embodiments described herein are used to explain the invention only, and do not limit the protection scope of the invention.

In order to better understand the invention, an application example of the automatic throat swab sampling system proposed by the invention is described in detail below.

Figure 1:
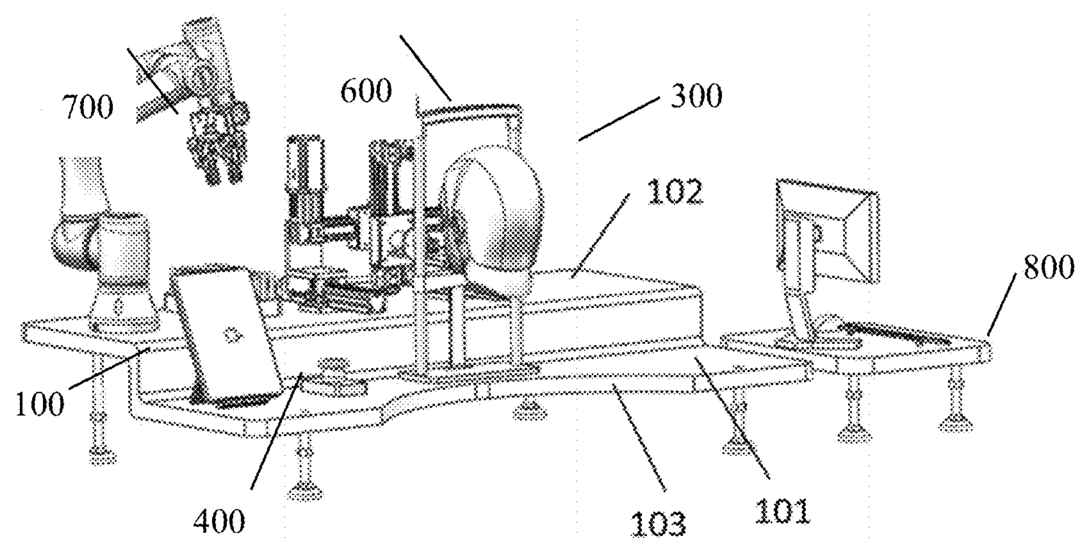
FIG. 1 is a three-dimensional view showing the overall structure of an automatic throat swab sampling system according to an embodiment of the invention.
Figure 2:
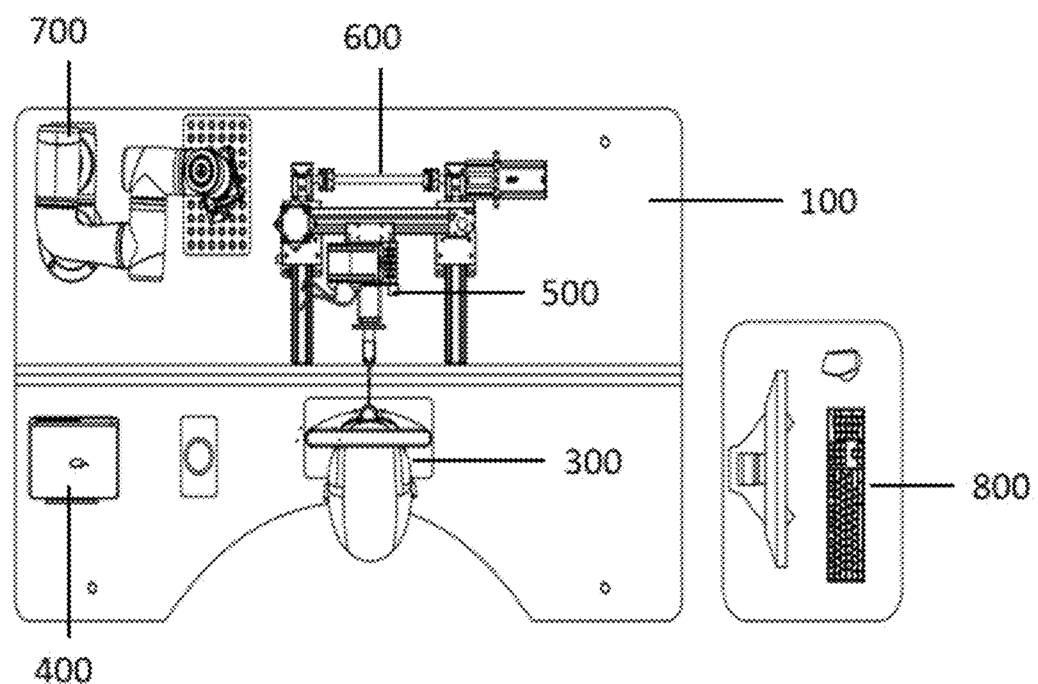
FIG. 2 is a top view of the automatic throat swab sampling system shown in FIG. 1

Referring to FIGS. 1 and 2, an autonomic throat swab sampling system according to one embodiment of the invention includes an automatic to-be-tested person identity information checking and collection prompting unit 400, a to-be-tested person head positioning unit 300, a navigation positioning unit 500, a sample collection execution unit 600, an automatic throat swab loading and unloading unit 700 and a remote monitoring unit 800 which are arranged on a working platform 100. During the sampling process, the autonomic throat swab sampling system can automatically check and confirm the patient's identity information, automatically load and unload the throat swab, can be seamlessly connected to an external sampling tube labeling system, a conveying system, and a sorting system; the autonomous trajectory planning and execution of the sampling action is simple to operate by ordinary remote on-duty personnel, saving the manpower of professional medical staff; and in addition, the system also has a flexible control sampling function to avoid hard stimulation on the throat tissue of the to-be-tested person.

The specific implementation and function of each component in this embodiment are described as follows:

As a supporting structure of the automatic throat swab sampling system, the working platform 100 is provided with a first working plane 101 and a second working platform 102, preferably, the first working plane 101 is lower than the second working platform 102. Both the automatic to-be-tested person identity information checking and collection prompting unit 400 and the to-be-tested person head positioning unit 300 are arranged on the first working plane 101, one side, towards the to-be-tested person, of the first working plane 101 is a circular-arc surface 103, so that the to-be-tested person head gets close to the 300 better; the navigation positioning unit 500, the sample acquisition execution unit 600 and the automatic throat swab loading and unloading unit 700 are arranged on the second working plane 102.

The automatic to-be-tested person identity information checking and collection prompting unit 400 includes an electronic screen (pad in this embodiment is adopted as the electronic screen), and the facial features of the to-be-tested person are acquired through a front camera of the electronic screen, and are compared with the identity information of the to-be-tested person for face recognition; the information of the to-be-tested person is shown to the tested person through the electronic screen for confirmation, the to-be-tested person is guided by voice and text prompts to enter automatic throat swab collecting equipment 600 after confirmation, and the operating procedures and precautions are reported.

Figure 3:
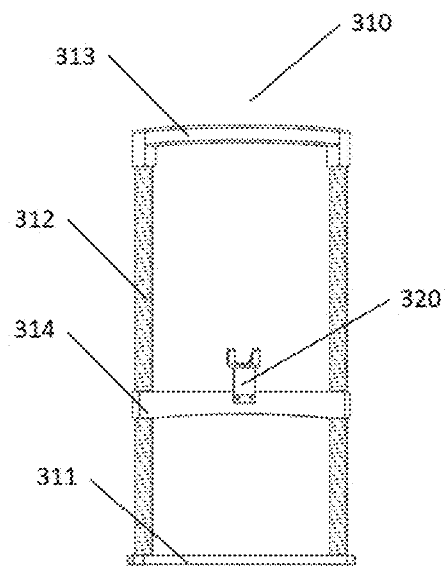
FIGS. 3 (*a*) and (*b*) are respectively a side view and a front view of the to-be-tested person head positioning unit in the automatic throat swab sampling system shown in FIG. 1.
Figure 3:
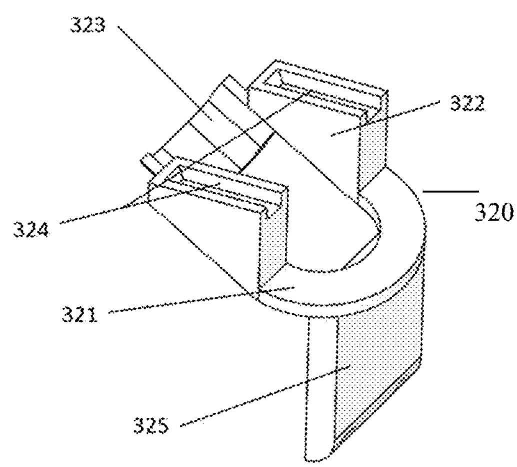

Referring to FIGS. 3 (*a*) and (*b*), the to-be-tested person head positioning unit 300 includes a head positioning frame 310 and a mouthpiece 320 fixedly arranged on the head positioning frame 310. The head positioning frame 310 includes a base 311 fixedly arranged on the middle of the first working plane 101, two screws 312 which are fixed to the base 311, jaw supports 314 which sleeve the two screws 312 through threads and a forehead support connected to the tops of the two screws 312; the distance from the jaw supports 314 and the mouthpiece 320 thereon to the base 311 is adjusted by rotating the jaw supports 314 on the screws 312, so that the mouthpiece 320 is positioned on a comfortable height of the to-be-tested person. The mouthpiece 320 includes a semicircular ring 312, an arc-shaped tongue pressing plate 323, two jaw opening pads 322 and a mouthpiece fixing plate 325 which are integrally formed, wherein the two jaw opening pads 322 are positioned between the semicircular ring 321 and the opening of the arc-shaped tongue pressing plate 323; the mouthpiece 320 is fixed to the jaw supports 314 through the mouthpiece fixing plate 325 via screws; specifically, the bottom of the semicircular ring 321 is fixed to the middle of the jaw supports 314 through the mouthpiece fixing plate 325 and the screw. To achieve convenient production and avoid cross-infection, the mouthpiece 320 is integrally made of a disposable consumable. The jaw opening pads 322 are integrally trapezoidal with trapezoidal surfaces facing upwards; alveolar sockets 324 are separately formed in side surfaces opposite to the inclined surfaces of the jaw opening pads 322 for allowing the to-be-tested person to bite. The arc-shaped tongue pressing plate 323 is matched with the oral cavity of the to-be-tested person in dimension for flattening the tongue of the patient to provide a clear space extending to the throat. The oral cavity of the to-be-tested person is opened by the mouthpiece 320 for allowing the sensor in the sample collection execution unit 600 and the throat swab tail end executor to enter the oral cavity; while the to-be-tested person keeps the mouthpiece 320 in mouth, the arc-shaped tongue pressing plate 323 gets close to the inner part of the oral cavity and presses the tongue to prevent the tongue from being bulged; the upper and lower alveolar sockets of the to-be-tested person bite jaw opening pads 322 which are trapezoidal, so that the mouth of the to-be-tested person is guaranteed to be opened to certain degree; the alveolar sockets are positioned on the upper and lower surfaces of the jaw opening pads 322 to be fixed, so that sliding is prevented; a front-end semicircular ring 321 abuts against lower front teeth and fixes the mouthpiece 320 in the depth direction of the oral cavity, so that the mouthpiece 320 is prevented from sliding out of the mouth. After the head positioning frame 310 is adjusted to the comfortable height of the to-be-tested person, approximate locations of five facial sense organs of the to-be-tested person are fixed, and the location of the oral cavity of the to-be-tested staff is found by image identification on a ToF sensor of the navigation positioning unit 500. After the location of the oral cavity of the to-be-tested person is found, the sample collection execution unit 600 moves a throat swab collection head to a position near the oral cavity for further precision operation.

The navigation positioning unit 500 includes a depth sensor which is fixedly arranged at the tail end of the sample collection execution unit 600, and is a ToF sensor; when the depth sensor moves into the oral cavity of the to-be-tested oral cavity along with the sample collection execution unit 600, the camera of the ToF sensor collects the real-time image inside the oral cavity and emits and modulates infrared light through the ToF sensor, and the reflected infrared light is received by a receiving module in the ToF sensor after being reflected by the throat. Modulated waves are emitted and received, and the camera of the ToF sensor can calculate the emitting and receiving phase difference to obtain a depth value, namely a depth distance between the camera and the throat through conversion, so that the image and depth information of the throat is obtained and transmitted to a remote monitoring unit 800 to process.

Figure 4:
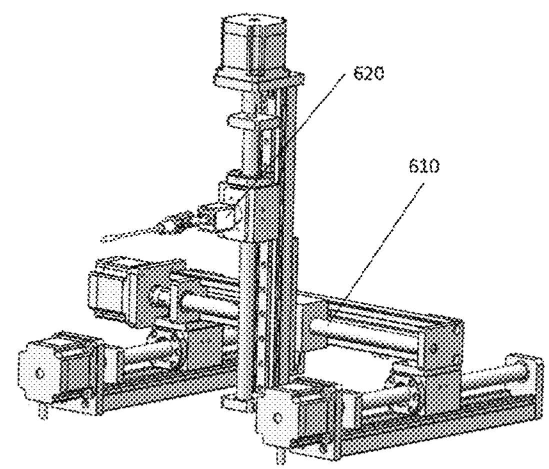
FIG. 4 (*a*)-(*d*) are schematic diagrams showing the structures of the guide rail type device and the tail end execution mechanism of the sample collection execution unit in the automatic throat swab sampling system shown in FIG. 1 respectively.
Figure 4:
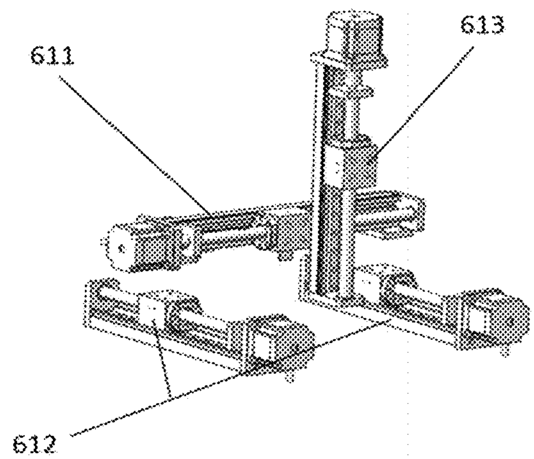
Figure 4:
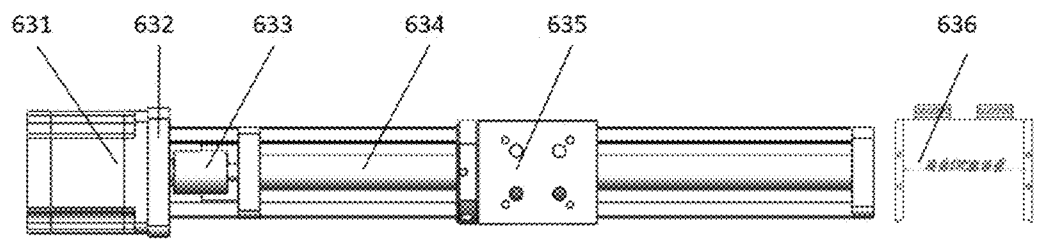
Figure 4:
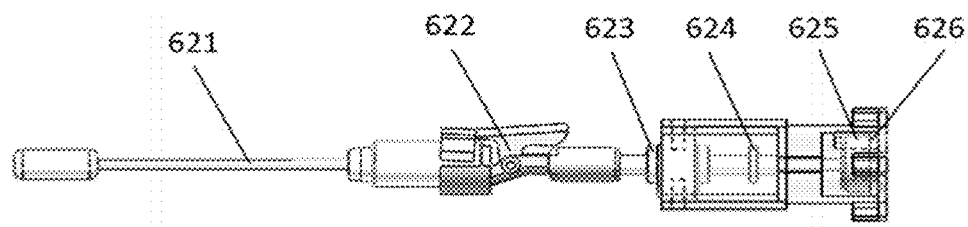

The sample collection execution unit 600 includes a three-degree-of-freedom guide rail type device 610 and a one-degree-of-freedom tail end execution mechanism 620, four freedom degrees in total, referring to FIGS. 4 (*a*) and (*b*). The axes in the width direction of the oral cavity, in the depth direction of the oral cavity and in the planar direction perpendicular to the working platform 100 are taken as X, Y and Z axes; the three-degree-of-freedom guide rail device 610 is a gantry type three-axis mechanism, including an X-axis module 611, two Y-axis modules 612 and a Z-axis module 613, which are completely the same in structure; one module is taken as an example for explanation, referring to FIG. 4(*c*), it includes a motor 631, a motor supporting plate 632 which is U-shaped, a shaft coupler 633, a rolling ball lead screw 634, a slide block 635 and a driver module 636 (adopting a Rockchip DK-1 digital type driver in the embodiment), where the motor 631 is fixed on one side wall of the motor supporting plate 632 through a screw, the output shaft of the motor 631 is connected to one end of the rolling ball lead screw 634 through the shaft coupler 633, the other end of the rolling ball lead screw 634 is fixed on the other side wall of the motor supporting plate 632, the slide block 635 sleeves the rolling ball lead screw 634, positive and negative rotation of the motor 631 is transmitted onto the rolling ball lead screw 634 through the shaft coupler 633, the rolling ball lead screw 634 drives the slide block 635 to do back-and-forth feeding motion, and the driver module 636 is connected to the input shaft of the motor 631. The two Y-axis modules are fixed on the second working plane 102 at intervals with spacing therebetween as the course of the rolling ball lead screw 634 in the X-axis module 612, and two side walls of the motor supporting plate 632 in the X-axis module 612 are fixedly connected to slide blocks 635 in the two Y-axis modules 612 through first connecting plates separately. The slide block in the Z-axis module 613 faces towards the oral cavity of the to-be-tested person, the bottom plate of the motor supporting plate 632 in the Z-axis module is fixedly connected to the slide block in the Y-axis module 612 through a second connecting plate, and the bottom side wall of the motor supporting plate 632 in the Z-axis module 613 is suspended on the second working plane 102, so that the Z-axis module 613 can move along the Y-axis with the slide block in the Y-axis module 612; in addition, the depth sensor in the navigation positioning unit 500 is further fixed on the slide block in the Z-axis module 613 through a connecting plate. The action of wiping the throat of the to-be-tested person is controlled by the X-axis module 611 and the Z-axis module 613, and feeding motion into the oral cavity of the to-be-tested person and axial feeding motion of the wiping action force control part are controlled by the Y-axis module 612; the X-axis module 611 and the Z-axis module 613 are linked to form the horizontal ring-shaped motion track. The main body part of the automatic throat swab sampling system realizes motion in each axial direction through the gantry type three-axis (X, Y and Z axes) mechanism which is controlled by a remote monitoring unit 800. The structure of the tail end execution mechanism 620 is as shown in FIG. 4) (d), which includes a swab clip 622, a linear slide rail 623, a pressure sensor 624, a linear servo motor 625 and a first control board 626, where the tail end of the swab clip 622 of the tail end execution mechanism 620 clips the throat swab 621, one side of the first control board 626 of the tail end execution mechanism 620 is connected to the slide block 635 of the Z-axis module 613 in the guide rail device 610 through a screw, and slides along with the slide block. The swab clip 622 is arranged at the foremost end of the linear servo motor 625 for clamping and fixing the throat swab 621. The linear slide rail 623 is arranged at the front end of the tail end execution mechanism 620 for guaranteeing smooth axial motion of the linear servo motor 625. The pressure sensor 624 is a one-dimensional force sensor which is arranged at the front end of the linear servo motor 625 for detecting the pressure value when the throat swab 621 is in contact with the soft tissue of the throat of the to-be-tested swab 621, and sending the received pressure value to the control board 626 in the form of a simulated signal. The linear servo motor 625 is a power unit which is fixedly arranged at the front end of the control board 626 for driving the throat swab 621 to move front and back in the axial direction. The first control board 626 is fixedly arranged at the tail end of the tail end execution mechanism 620, a power supply, an operational amplifier circuit, a first control chip TMS320F28377 and an ADC chip are integrated on the first control board 626 for providing power to the pressure sensor and acquiring output axial pressure simulated signal ADC of the throat swab 621, which is converted into an axial pressure digital signal of the throat swab 621 after being operationally amplified and filtered; the digital signal is collected by the first control chip which compares it with location information of the linear servo motor 625; the PID controller performs adjustment control on the linear servo motor 625 which moves to drive forward-retract motion of the throat swab 621 to adjust the pressure value when the throat swab 621 is in contact with the soft tissue of the throat of the to-be-tested person. The first control chip sends the collected axial pressure digital signal of the throat swab, and the location and rotation speed information of the linear servo motor 625 to the remote monitoring unit 800 through the serial port, and the real-time state of the tail end execution mechanism 620 is obtained by data reading and storage.

The automatic throat swab loading and unloading unit 700 includes a six-degree-of-freedom mechanical arm (JAKAzu3 six-degree-of-freedom mechanical arm developed by the JAKA company in the embodiment) which is controlled to reach the designated position of the throat swab and a tail end gripping claw which is opened and closed to grip the throat swab; and the JAKAzu3 six-degree-of-freedom mechanical arm gripping the throat swab is controlled to load to the tail end execution mechanism 620 in the sample collection execution unit 600.

Figure 5:
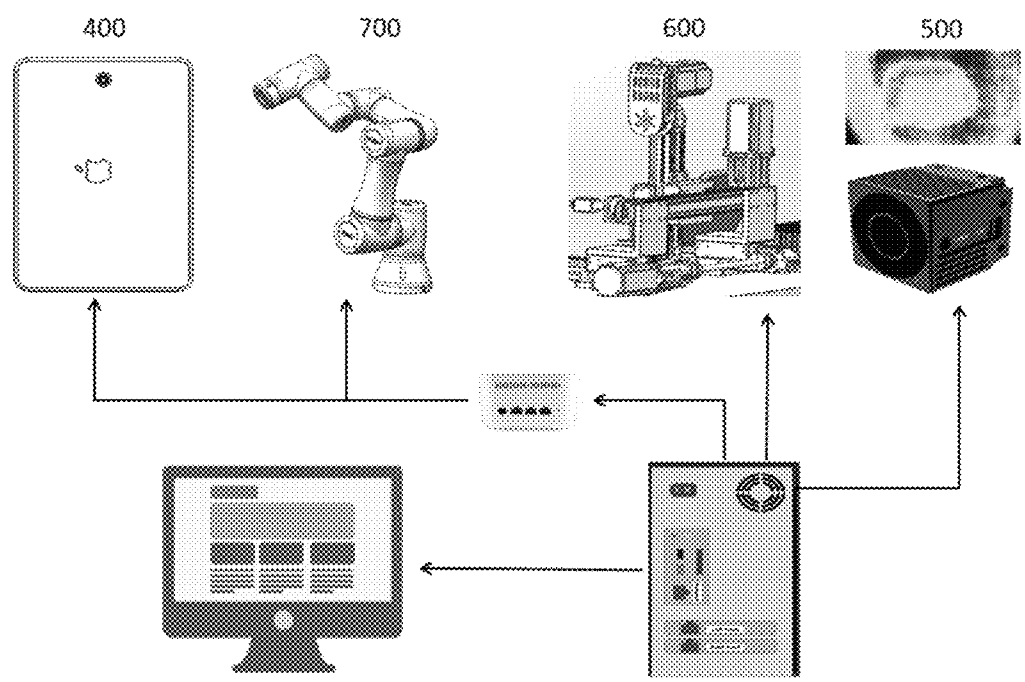
FIG. 5 is a schematic diagram showing the system architecture of the automatic throat swab sampling system.

The remote monitoring unit 800 mainly comprises a master control system in which an information base of the to-be-tested person is stored, and a second control chip (the second control chip adopting a STM32H743 single chip microcomputer in the embodiment), which communicates with the PC through a RS-485 interface is integrated on the second control board in a PC of the master control system. The automatic to-be-tested person identity information checking and collection prompting unit 400 and the automatic throat swab loading the unloading unit 700 communicate with the PC of the master control system through a TCP network; the sample collection execution unit 600 communicates with the PC of the master control system through the RS-485 interface, the navigation positioning unit 500 communicates with the PC of the master control system through USB; in a throat swab collecting process, the real-time information of all units communicates with the remote monitoring unit, and medical staff monitors the collected person and all the units in real time through a computer in a remote safety room, so that measures can be taken timely to guarantee safety and effectiveness of the whole process when an accident occurs. Specifically referring to FIG. 5, the automatic to-be-tested person identity information checking and collection prompting unit 400 and the automatic throat swab loading and unloading unit 700 communicate with the PC of the master control system through the TCP network, the to-be-tested person identity information base in the master control system accomplishes checking confirmation of person information by the automatic to-be-tested person identity information checking and collection prompting unit 400, and the PC in the master control system controls the automatic throat swab loading and unloading unit 700 to realize automatic loading and unloading task of the throat swab through the TCP network. Each driver module in the sample collection execution unit 600 and the second control board are in communication through a GIOP (General-purpose input/output) interface, and are in communication with the PC of the master control system through a RS-485 interface; the navigation positioning unit 500 is connected to the PC of the master control system through USB for transmitting image and depth information collected by the depth sensor onto the PC of the master control system; due to the influences from the external environment, the depth sensor will have certain disturbance noises in the collecting process, so that the image and depth information is affected to certain extent; and the remote monitoring unit 800 accurately calculates the location information of tonsil at the two sides in the oral cavity of the to-be-tested person after the image and depth information collected by the depth sensor is denoised while compensated through a mean filter algorithm, and carries out coordinate conversion on the location information of the tonsil at the two sides obtained by the depth sensor to match with a coordinate system of the sample collection execution unit 600 which is guided to the location for specific sample collection. the second control chip performs multitask dispatch needed for motion calculation and trajectory tracking of the gantry type three-axis mechanism by internally operating an Free-RTOS operation system, where the dispatch processes and converts the image and depth information collected by the depth sensor into mechanical motion (the publicly known technology of the field) of the gantry type three-axis mechanism in real time, and sends a corresponding control signal to each driver module in the sample collection execution unit 600 through the GPIO interface, there are three control signals in total (two Y-axis modules 612 sharing one signal, and X-axis module 611 and Z-axis module 613 being each controlled by one signal), and each control signal separately includes PWM (Pulse Width Modulation), direction and enabling signals for controlling motor in the module of each axis. The second control chip in the PC of the remote monitoring unit 800 communicates with the first control chip in the tail end execution mechanism 620 through a serial interface, and the second control chip reads and stores the throat swab 621 axial pressure digital signal collected by the first control chip, and the location and rotation speed information of the linear servo moor 625 to obtain the real-time state of the tail end execution mechanism 620.

The invention and its embodiments are schematically described above, and the description is not restrictive. What is shown in the drawings is only one of the embodiments of the invention, and is not limited to this in practice. Therefore, if a person of ordinary skill in the art receives its enlightenment and does not deviate from the inventive purpose of the present invention, without creatively designing a manner and embodiment similar to the technical solution, it shall fall within the protection scope of the invention.

What is claimed is:

1. An autonomic throat swab sampling system, comprising an automatic to-be-tested person identity information checking and collection prompting unit (400), a to-be-tested person head positioning unit (300), a navigation positioning unit (500), a sample collection execution unit (600), an automatic throat swab loading and unloading unit (700) and a remote monitoring unit (800) which are arranged on a working platform (100), wherein the automatic to-be-tested person identity information checking and collection prompting unit (400) comprises an electronic screen, and the facial features of the to-be-tested person are acquired through a front camera of the electronic screen, and are compared with the identity information of the to-be-tested person for face recognition; the information of the to-be-tested person is shown to the tested person through the electronic screen for confirmation, the to-be-tested person is guided by voice and text prompts to enter automatic throat swab collecting equipment (600) after the confirmation, and the operating procedures and precautions are reported;

the to-be-tested person head positioning unit (300) comprises a head positioning frame (310), through which the head of the to-be-tested person is fixed, and a mouthpiece (320) fixedly arranged thereon, where the mouthpiece (320) is positioned at comfortable height of the to-be-tested person by adjusting a distance between the mouthpiece (320) and the working platform (100), is made of a disposable consumable, and is used for opening the oral cavity of the to-be-tested person and flattening the tongue of the to-be-tested person to provide a clear space extending to the throat;

the navigation positioning unit (500) comprises a depth sensor fixed at the tail end of the sample collection execution unit (600), which enters the oral cavity of the to-be-tested person along with the sample collection execution unit (600) to collect a throat image and determine depth information between the depth sensor and the throat of the to-be-tested person;

the sample collection execution unit (600) comprises a three-degree-of-freedom guide rail type device (610) and a one-degree-of-freedom end execution mechanism (620), wherein the three-degree-of-freedom guide rail type device (610) is a gantry type three-axis mechanism having X, Y and Z axes in a width direction of the oral cavity, a depth direction of the oral cavity and a planar direction perpendicular to the working platform (100); the gantry type three-axis mechanism includes an X-axis module (611), two Y-axis modules (612) which are fixedly arranged on the working platform (100) at intervals and a Z-axis module (613), the Y-axis module (612), the X-axis module (611) and the Z-axis module (613) are sequentially connected and linked with one another; the depth sensor in the navigation positioning unit (500) and the tail end execution mechanism (620) are fixedly arranged on the Z-axis module (613); and the action of wiping the throat of the to-be-tested person is controlled by the X-axis module (611) and the Z-axis module (613), and the feeding motion into the oral cavity of the to-be-tested person and the axial feeding motion of the wiping action force control part are controlled by the Y-axis module (612);

the automatic throat swab loading and unloading unit (700) comprises a six-degree-of-freedom mechanical arm which is controlled to reach the designated position of the throat swab and a tail end gripping claw which is opened and closed to grip the throat swab; and the six-degree-of-freedom mechanical arm gripping the throat swab is controlled to load to the tail end execution mechanism (620) in the sample collection execution unit (600);

the remote monitoring unit (800) comprises a master control system in which an information base of the to-be-tested person is stored, wherein a second control chip, which communicates with the PC through a RS-485 interface is integrated on a second control board in a PC of the master control system; the automatic to-be-tested person identity information checking and collection prompting unit (400) and the automatic throat swab loading the unloading unit (700) communicate with the PC of the master control system through a TCP network; the to-be-tested person identity information base in the master control system accomplishes the checking confirmation of person information by the automatic to-be-tested person identity information checking and collection prompting unit (400); the navigation positioning unit (500) is connected to the PC of the master control system through USB for transmitting the collected image and depth information of the depth sensor onto the PC of the master control system; the location information of tonsil at the two sides in the oral cavity of the to-be-tested person is accurately calculated after the image and depth information collected by the depth sensor is denoised while compensated through a mean filter algorithm, and then is subjected to coordinate conversion for being matched with a coordinate system of the sample collection execution unit (600) which is guided to the location to collect samples; the guide rail type device (610) in the sample collection execution unit (600) is separately connected to the PC of the master control system through a RS-485 interface and a GPIO interface; the second control chip performs the multitask dispatch needed for motion calculation and trajectory tracking of the gantry type three-axis mechanism, wherein the dispatch processes and converts the image and depth information collected by the depth sensor into mechanical motion of the gantry type three-axis mechanism in real time, and sends a corresponding control signal to the module of each axis in the sample collection execution unit (600) through the GPIO interface; and the tail end execution mechanism (620) in the sample collection execution unit (600) is connected to the PC of the master control system through a serial interface to obtain a real-time state of the tail end execution mechanism (620).

2. The autonomic throat swab sampling system according to claim 1, wherein each control signal separately comprises PWM (Pulse Width Modulation), direction and enabling signals for controlling the module of each axis.

3. The autonomic throat swab sampling system according to claim 1, wherein in the to-be-tested person head positioning unit (300), the head positioning frame (310) comprises a base (311) fixedly arranged on the working plane (100), two screws (312) fixed to the base (311), a jaw support (314) sleeving the two screws (312) and a forehead neck (313) connected to the tops of the two screws (312), the jaw support (314) and a distance from a mouthpiece (320) on the jaw support to the base (311) are adjusted by rotating the jaw support (314) on the screws (312);

the mouthpiece (320) comprises a semicircular ring (321), an arc-shaped tongue pressing plate (323), two jaw opening pads (322), which are positioned between the semicircular ring (321) and the opening of the arc-shaped tongue pressing plate (323) and a mouthpiece fixing plate (325), which are integrally formed; the mouthpiece (320) is fixed to the jaw support (314) through the mouthpiece fixing plate (325); the jaw opening pads (322) are integrally trapezoidal with forward trapezoidal inclined surfaces; alveolar sockets (324) are separately formed in the inclined surface of each jaw opening pad (322) and the side surface opposite to the inclined surface for allowing the tested person to bite; the arc-shaped tongue pressing plate (323) is matched with the oral cavity of the to-be-tested person in dimension; and after the to-be-tested person keeps the mouthpiece (320) in mouth, the arc-shaped tongue pressing plate (323) is close to the inner part of the oral cavity.

4. The autonomic throat swab sampling system according to claim 1, wherein in the sample collection execution unit (600), the structure of the module of each is the same, and separately comprises a motor (631), a motor supporting plate (632), a shaft coupler (633), a rolling ball lead screw (634), a slide block (632) and a driver module (636), the motor supporting plate (632) is U-shaped, the motor (631) is fixed on one side wall of the motor supporting plate (632), the output shaft of the motor (631) is connected to one end of the rolling ball lead screw (634) through the shaft coupler (633), the other end of the rolling ball lead screw (634) is fixed on the other side wall of the motor supporting plate (632), the slide block (632) sleeves the rolling ball lead screw (634), the driver module (636) is connected to the input shaft of the motor (631); and the driver module in the module of each axis is separately connected to the second control chip through a GPIO interface;

the two Y-axis modules (612) are fixed on the working plane (100) at intervals with spacing therebetween as the course of the rolling ball lead screw in the X-axis module (611), and two side walls of the motor supporting plate in the X-axis module (611) are fixedly connected to slide blocks in the two Y-axis modules (612) through first connecting plates separately; the slide block in the Z-axis module (613) faces towards the oral cavity of the to-be-tested person, the bottom plate of the motor supporting plate in the Z-axis module (613) is fixedly connected to the slide block in the Y-axis module (612) through a second connecting plate, and the bottom side wall of the motor supporting plate in the Z-axis module (613) is suspended on the second working plane (100), so that the Z-axis module (613) can move along the Y-axis with the slide block in the Y-axis module (612); a depth sensor in the navigation positioning unit (500) is further fixed on the slide block in the Z-axis module (613) through a third connecting plate.

5. The autonomic throat swab sampling system according to claim 4, wherein the tail end execution mechanism (620) comprises a swab clip (622) which is arranged at the foremost end of a linear servo motor (625), a linear slide rail (623), a pressure sensor (624), the linear servo motor (625) and a first control board (626); the tail end of the swab clip (622) clips the throat swab (621), one side of the first control board (626) is connected to the slide block in the Z-axis module (613) and slides along with the slide block; the pressure sensor (624) is arranged at the front end of the linear servo motor (625) for detecting the pressure value when the throat swab (621) is in contact with the soft tissue of the throat of the to-be-tested swab, and sending the received pressure value to the control board (626) in the form of a simulated signal; the linear servo motor (625) is fixedly arranged at the front end of the control board (626) for driving the throat swab (621) to move front and back in the axial direction; a power supply, an operational amplifier circuit, a first control chip and an ADC chip are integrated on the first control board (625) to provide power to the pressure sensor and collect the output throat swab axial pressure simulated signal ADC which is converted into the throat swab axial pressure digital signal for being collected by the first control chip after being subjected to operational amplifying and filtered; and the first control chip compares the digital signal with location information of the linear servo motor (625) and then the linear servo motor (625) is subjected to adjustment control through the PID controller; the first control chip sends the collected throat swab axial pressure digital signal, and location and rotation speed information of the linear servo motor (625) to the remote monitoring unit (800), and the real-time state of the tail end execution mechanism 620 is obtained by data reading and storage.

6. The autonomic throat swab sampling system according to claim 5, wherein the pressure sensor (624) is a one-dimensional force sensor.

* * * * *